US 12,383,130 B2

(12) United States Patent
Fukuma et al.

(10) Patent No.: US 12,383,130 B2
(45) Date of Patent: Aug. 12, 2025

(54) OPHTHALMOLOGIC APPARATUS

(71) Applicant: Topcon Corporation, Tokyo (JP)

(72) Inventors: Yasufumi Fukuma, Tokyo (JP);
Zhenguo Wang, Ridgewood, NJ (US);
Zaixing Mao, Harrison, NJ (US);
Kazuhiro Oomori, Tokyo (JP);
Makoto Fujino, Tokyo (JP)

(73) Assignee: Topcon Corporation, Tokyo (JP)

( * ) Notice: Subject to any disclaimer, the term of this patent is extended or adjusted under 35 U.S.C. 154(b) by 910 days.

(21) Appl. No.: 17/594,912

(22) PCT Filed: Apr. 24, 2020

(86) PCT No.: PCT/JP2020/017834
§ 371 (c)(1),
(2) Date: Aug. 15, 2022

(87) PCT Pub. No.: WO2020/226082
PCT Pub. Date: Nov. 12, 2020

(65) Prior Publication Data
US 2022/0395175 A1 Dec. 15, 2022

Related U.S. Application Data

(60) Provisional application No. 62/844,794, filed on May 8, 2019.

(51) Int. Cl.
*A61B 3/107* (2006.01)
*A61B 3/00* (2006.01)
(52) U.S. Cl.
CPC ............ *A61B 3/107* (2013.01); *A61B 3/0008* (2013.01)

(58) Field of Classification Search
CPC .............................. A61B 3/107; A61B 3/0008
(Continued)

(56) References Cited

U.S. PATENT DOCUMENTS 8,953,172 B2 * 2/2015 Kawano ............. G01N 21/4795
356/497
2002/0048025 A1 * 4/2002 Takaoka ............. G01N 21/4795
356/497

(Continued)

FOREIGN PATENT DOCUMENTS

JP          3586039 B2     11/2004

OTHER PUBLICATIONS

International Search Report and Written Opinion mailed Jul. 7, 2020, in connection with International Patent Application No. PCT/JP2020/017834, filed Apr. 24, 2020, 8 pgs. (including translation).

*Primary Examiner* — Sharrief I Broome
(74) *Attorney, Agent, or Firm* — Chiesa Shahinian & Giantomasi PC

(57) ABSTRACT

An ophthalmologic apparatus includes an objective lens that faces a subject's eye, an illumination optical system that irradiates a cornea of the subject's eye with illumination light through the objective lens, and a corneal measurement optical system including an interference image capturing camera that takes an image of a corneal reflection light. The corneal reflection light is a reflection of the illumination light reflected from the cornea, through the objective lens. A numerical aperture G of the illumination optical system is larger than a numerical aperture g of the corneal measurement optical system.

4 Claims, 3 Drawing Sheets

(58) Field of Classification Search
USPC .......................................................... 351/221
See application file for complete search history.

(56) References Cited

U.S. PATENT DOCUMENTS

2014/0016136 A1\* 1/2014 Kawano ............. G01B 9/02044
356/479
2017/0224208 A1\* 8/2017 Bublitz .............. G01B 9/02032

\* cited by examiner

OPHTHALMOLOGIC APPARATUS

CROSS-REFERENCE TO RELATED APPLICATIONS

This application is a national stage of International Patent Application Serial No. PCT/JP2020/017834 filed Apr. 24, 2020, which claims priority to U.S. Provisional Patent Application No. 62/844,794 filed May 8, 2019, the disclosures of both are incorporated herein by reference in their entirety.

TECHNICAL FIELD

The present disclosure relates to an ophthalmologic apparatus, and more particularly, to an ophthalmologic apparatus that examines states of an anterior segment and tear fluid film of a subject's eye.

BACKGROUND ART

There has been known an ophthalmologic apparatus that irradiates a cornea of a subject's eye with illumination light, and observes a state of an anterior segment and an interference image formed by a tear fluid film of the cornea of the subject's eye to make a diagnosis of dry eye, for example.

For example, it has been known that the anterior segment is successfully observed or photographed when a light beam is allowed to enter the cornea through a light projection system (illumination optical system) in a direction perpendicular to a corneal surface so that the reflection from the cornea is efficiently condensed (Patent Document 1).

CITATION LIST

Patent Document

Patent Document 1: Japanese Patent No. 3586039

SUMMARY OF THE INVENTION

Technical Problem

However, Patent Document 1 does not specify numerical apertures of the light projection system and a corneal measurement system for the interference image formed by the tear fluid film, and thus, has not been a technique that permits variation in eye shape for each subject and incomplete alignment, while improving the capability of interference image observation.

It is an object of the present disclosure to provide an ophthalmologic apparatus that attempts to optimize a numerical aperture (NA) of an illumination optical system and a numerical aperture of a corneal measurement optical system, and improves a measurement accuracy while permitting variation in subject's eye shape and incomplete alignment.

Solution to the Problem

An ophthalmologic apparatus of the present disclosure is an ophthalmologic apparatus including: an objective lens that faces a subject's eye; an illumination optical system that irradiates a cornea of the subject's eye with illumination light through the objective lens; and a corneal measurement optical system that takes an image of a corneal reflection light, which is a reflection of the illumination light reflected from the cornea, through the objective lens. A numerical aperture G of the illumination optical system is larger than a numerical aperture g of the corneal measurement optical system.

Advantages of the Invention

The present disclosure can provide an ophthalmologic apparatus that attempts to optimize a numerical aperture of an illumination optical system and a numerical aperture of a corneal measurement optical system, and improves a measurement accuracy while permitting variation in subject's eye shape and incomplete alignment.

DESCRIPTION OF EMBODIMENTS

Figure 1:
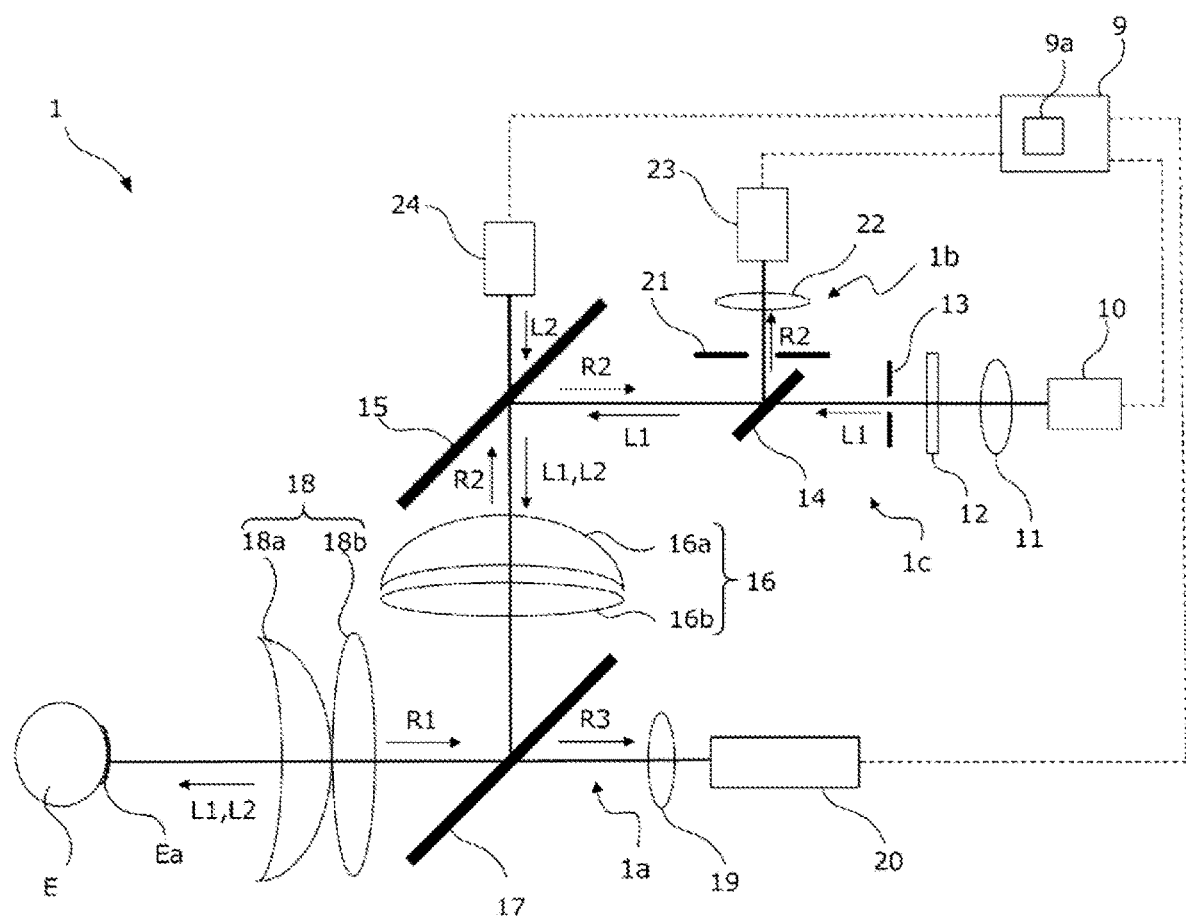
FIG. 1 is a schematic view illustrating an optical system of an ophthalmologic apparatus according to an embodiment of the present disclosure.

FIG. 1 is a schematic view illustrating an optical system of an ophthalmologic apparatus 1 according to an embodiment of the present disclosure. The optical system of the ophthalmologic apparatus 1 includes an anterior segment observation optical system 1a, a corneal measurement optical system 1b, and an illumination optical system 1c.

The anterior segment observation optical system 1a includes a first lens group 18 of the present disclosure. The anterior segment observation optical system 1a includes a third half mirror 17, an anterior segment lens 19, and an anterior segment camera 20 that are arranged along the direction of an optical axis of the first lens group 18.

The first lens group 18 is a so-called objective lens. In the present embodiment, the objective lens (first lens group 18) includes a plurality of lenses (18a, 18b), but the objective lens may include a single lens only. The first lens group 18 is capable of causing the illumination light incident from the illumination optical system 1c to irradiate the corneal surface of the cornea Ea of the subject's eye E via the third half mirror 17. Corneal reflection light, which is the reflection of the illumination light from the corneal surface, enters the first lens group 18. This corneal reflection light enters the third half mirror 17 from the first lens group 18.

The third half mirror 17 allows part of the corneal reflection light incident from the first lens group 18 to pass therethrough and exit therefrom toward the anterior segment lens 19, and reflects the rest of the corneal reflection light toward a second lens group 16, which will be described later.

The anterior segment lens 19 allows the corneal reflection light incident from the first half mirror 17 to pass therethrough and exit therefrom toward the anterior segment camera 20. The anterior segment camera 20 includes a complementary metal oxide semiconductor (CMOS) or charge coupled device (CCD) imaging element, and takes an image of the corneal reflection light incident from the anterior segment lens 19 to output an imaging signal of an observation image of an anterior segment of the subject's eye E (will be hereinafter referred to as an "anterior segment observation image") to a control unit 9.

The illumination optical system 1c forms an optical path branching from the anterior segment observation optical system 1a via the third half mirror 17.

The illumination optical system 1c includes an illumination light source 10. The illumination optical system 1c further includes an illumination system lens 11, a filter 12, an illumination system diaphragm 13, a first half mirror 14, a second half mirror 15, and a second lens group 16 which are arranged on an optical path of illumination light emitted from the illumination light source 10. The illumination optical system 1c shares the first half mirror 17 and the first lens group 18 with the anterior segment observation optical system 1a.

The illumination light source 10 is a light source that emits light. The illumination light source 10 may be, for example, a light emitting diode (LED) light source or halogen lamp which emits white light, and emits white light as illumination light L1 toward the lens 11. Alternatively, an LED having a different wavelength, a laser light source, or a combination of them may also be used. The illumination system lens 11 allows the illumination light L1 incident from the illumination light source 10 to exit therefrom toward the filter 12. The filter 12 adjusts the light intensity and/or wavelength distribution of the illumination light entered from the illumination system lens 11, and allows the adjusted illumination light L1 to exit therefrom toward the illumination system diaphragm 13. The illumination system diaphragm 13 emits the illumination light L1 entered from the filter 12 toward the first half mirror 14.

The first half mirror 14 reflects part of the corneal reflection light (R2) incident from the second lens group 16, which will be described later, toward the corneal measurement optical system 1b. The first half mirror 14 is capable of allowing part of the illumination light L1 incident from the filter 12 to pass therethrough and exit therefrom toward the second half mirror 15.

The second half mirror 15 and the second lens group 16 allow the illumination light L1 incident from the first half mirror 14 to exit therefrom toward the third half mirror 17 described above, and allow the corneal reflection light R2 incident from the third half mirror 17 to exit therefrom toward the first half mirror 14.

The illumination light L1 emitted from the illumination light source 10 irradiates the corneal surface of the cornea Ea through the first lens group 18 after passing through the illumination system lens 11 and the third half mirror 17. As a result, the corneal reflection light R1, which is the reflection of the illumination light L1 reflected from the corneal surface, can enter the first lens group 18.

It will be described below a numerical aperture G of the illumination optical system 1c. As described above, the illumination optical system 1c of the present disclosure includes the following optical elements, namely, the illumination light source 10, the illumination system lens 11, the filter 12, the illumination system diaphragm 13, the first half mirror 14, the second half mirror 15, the second lens group 16, the third half mirror 17, and the first lens group 18. These optical elements are configured such that the illumination optical system 1c has a numerical aperture G of approximately 0.10. The illumination optical system 1c shares the optical elements from the third half mirror to the first lens group 18 with the corneal measurement optical system 1b. Thus, the numerical aperture G can be set through appropriate selection of the optical characteristics, such as an aperture, of the illumination system lens 11 and the illumination light source 10, in particular. The numerical aperture G can be set through adjustment of an aperture of the illumination system diaphragm 13.

The corneal measurement optical system 1b forms an optical path branching from the illumination optical system 1c via the first half mirror 14. The corneal measurement optical system 1b shares the optical elements from the first lens group 18 to the first half mirror 14 with the illumination optical system 1c, and also includes a corneal measurement system diaphragm 21, a corneal measurement system lens 22, and an interference image capturing camera 23.

The corneal measurement system diaphragm 21 and the corneal measurement system lens 22 allow the corneal reflection light R2 incident from the first half mirror 14 to exit therefrom toward the interference image capturing camera 23.

The interference image capturing camera 23 includes a CMOS or CCD imaging element, and takes an image of the corneal reflection light R2 incident from the lens 22 to output an imaging signal of a corneal reflection image to the control unit 9.

It will be described below a numerical aperture g of the corneal measurement optical system 1b. As described above, the corneal measurement optical system 1b of the present disclosure includes the following optical elements, namely, the interference image capturing camera 23, the corneal measurement system lens 22, the corneal measurement system diaphragm 21, the first half mirror 14, the second half mirror 15, the second lens group 16, the third half mirror 17, and the first lens group 18. These optical elements are configured such that the corneal measurement optical system 1b has a central value of the numerical aperture g of approximately 0.03. The corneal measurement optical system 1b shares the optical elements from the first half mirror 14 to the first lens group 18 with the illumination optical system 1c. Thus, the numerical aperture g is set through appropriate selection of the optical characteristics of the corneal measurement system lens 22 and the interference image capturing camera 23, in particular. Further, the numerical aperture g can be set through adjustment of an aperture of the corneal measurement system diaphragm 21. Note that the numerical aperture g can be set to 0.01 to 0.06 for a reason described later. From the viewpoint of the accuracy of detection of a tear fluid film based on a focal depth and wavelength characteristics of the interference image, the numerical aperture g is desirably 0.02 to 0.05.

A fixation lamp 24 is a light source that fixes the position of the subject's eye E by guiding the subject's gaze for accurate observation and photographing of the state of the subject's eye E. A light emitting diode (LED) light source, or a halogen lamp can be used as the fixation lamp 24. Fixation light L2 emitted from the fixation lamp 24 passes through the second half mirror 15 and the second lens group 16, is reflected from the third half mirror 17, and enters the subject's eye E through the first lens group 18.

The control unit 9 is electrically connected to the illumination light source 10, the anterior segment camera 20, the interference image capturing camera 23, and the fixation lamp 24.

The control unit 9 includes a computing unit 9a. The computing unit 9a detects wavelength characteristics of the interference image at each position of the corneal reflection image based on the inputted image data of the corneal reflection light R2 (corneal reflection image). Accordingly, the thickness of the tear fluid film at each position on the corneal surface can be detected. The tear fluid film herein refers to an oil layer (lipid layer), an aqueous layer, and a mucinous layer, or a combination of these layers.

Figure 2:
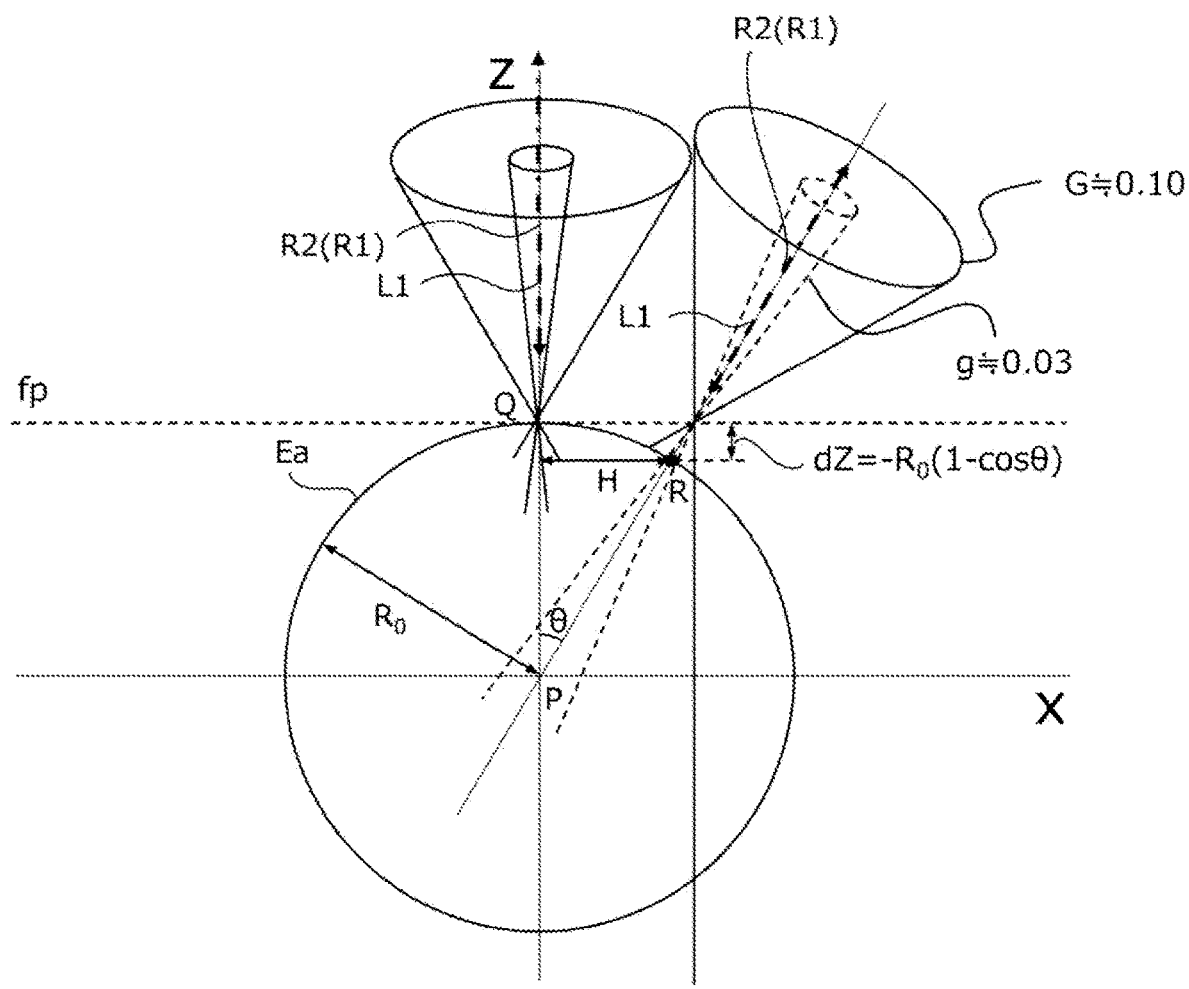
FIG. 2 is a schematic view illustrating a relationship among a cornea, illumination light, and corneal reflection light according to the embodiment of the present disclosure.
Figure 3:
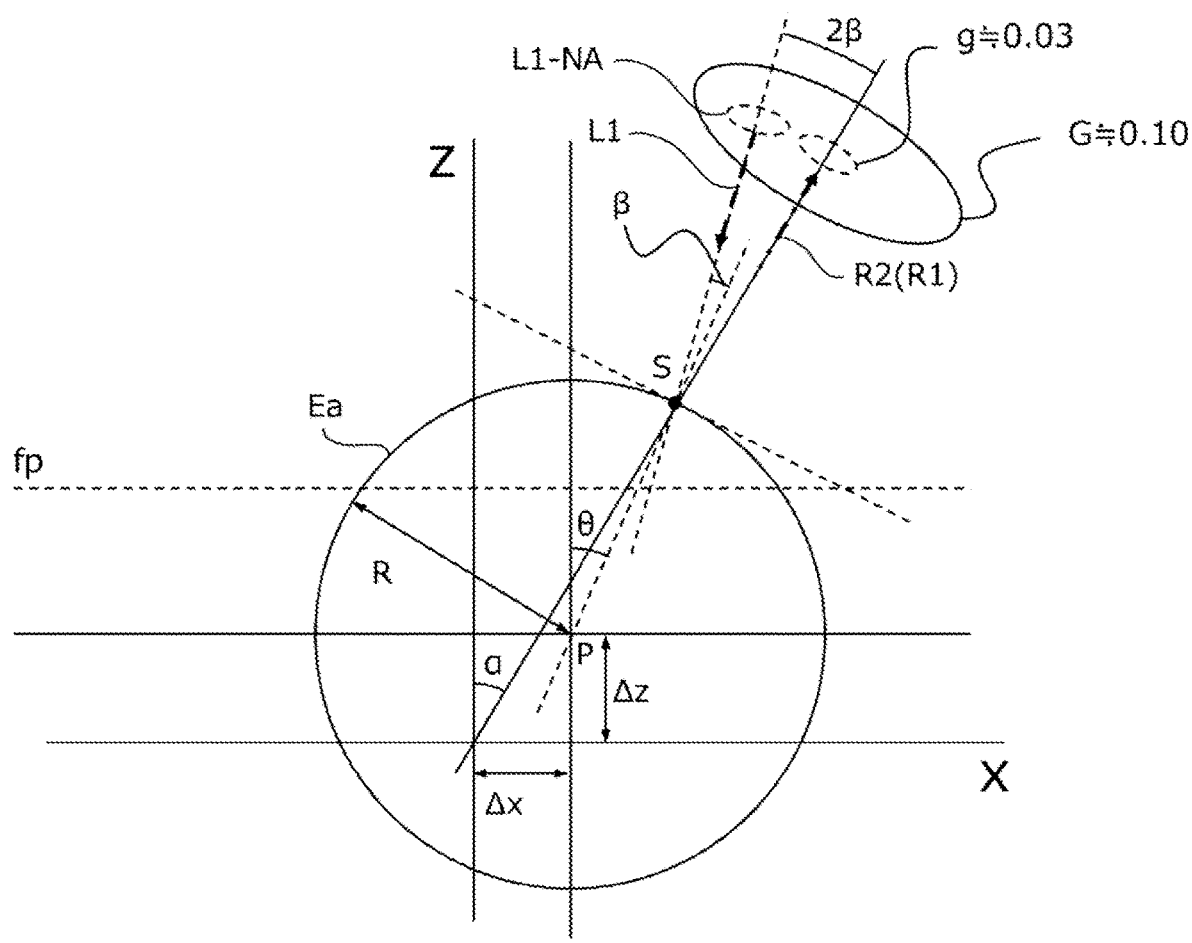
FIG. 3 is a schematic view illustrating a relationship among a cornea, illumination light, and corneal reflection light according to the embodiment of the present disclosure.

Referring to FIGS. 2 and 3, it will be described below a relationship among the cornea, the illumination light, and the corneal reflection light according to the embodiment of the present disclosure. FIG. 2 illustrates a state where the ophthalmologic apparatus 1 and the subject's eye E are in an ideal positional relationship, i.e., they are in proper alignment. FIG. 3 illustrates a state where the ophthalmologic apparatus 1 and the subject's eye E are shifted in position from each other, i.e., they are in misalignment.

Referring to FIG. 2, it will be described below the state where the ophthalmologic apparatus 1 and the subject's eye E are in the ideal positional relationship, i.e., they are in proper alignment. FIG. 2 assumes that the cornea Ea of the subject's eye E is a sphere having a radius $R_0$. The radius $R_0$ of the cornea Ea is approximately 7.7 mm. In FIG. 2, a front direction of the subject's eye E is defined as a Z-axis, and an axis orthogonal to the Z-axis as an X-axis. Of the illumination light L1 entering the surface of the cornea Ea from the first lens group 18, part that contributes to corneal observation is denoted by L1' and of the corneal reflection light R1 reflected from the cornea Ea, part of the corneal reflection light reaching the interference image capturing camera 23 of the corneal measurement optical system 1b is referred to as the corneal reflection light R2.

In FIG. 2, the cornea Ea is assumed to be a sphere, and the alignment is appropriate. Thus, the center of light flux of the illumination light L1 focusing on the first lens group 18 passes through the center the center of the sphere formed by the cornea Ea. Thus, in FIG. 2, the illumination light L1 has an optical axis passing through the radial center P of the cornea Ea, and the corneal reflection light R2 is reflected in a normal direction of a tangent line of the cornea E1 with respect to a point Q at which the illumination light L1 enters the cornea E1, i.e., in a direction that is 180-degree opposite to the illumination light L1. Since L1' is present at the center of the aperture of the illumination light L1, the corneal reflection light R2 reflected from the cornea can exist within the aperture.

In FIG. 2, the illumination light incident from the Z-axis direction is aligned to be focused on a vertex portion of the cornea Ea, thereby forming a focal plane (focusing plane) fp at the vertex portion of the cornea Ea. Since the illumination light L1 expands to some extent, the illumination light L1' that enters from a position shifted from the Z-axis in the X-axis direction by a distance H has an incident angle θ, and a defocus amount dZ between the surface of the cornea Ea and the focal plane fp is represented by the following formula:

$$dZ = -R_0(1-\cos \theta).$$

Hence, the numerical aperture g of the corneal measurement optical system 1b is desirably set to be somewhat small so that the interference image capturing camera 23 can capture an image even if the corneal reflection light R2(R1) is reflected with the above-mentioned defocus amount dZ.

Next, referring to FIG. 3, it will be described below a state where the ophthalmologic apparatus 1 and the subject's eye E are shifted in position from each other, i.e., a state in which they are in misalignment, or the alignment is incomplete. The shape of the subject's eye E, i.e., an eyeball of a human (human eye), is different for each person, and the curvature of the cornea Ea also varies for each person. In addition, vertical and horizontal curvatures of the same subject are generally different, and the shape of the eye is not always a perfect sphere. This results directly or indirectly in incomplete alignment. Further, the ophthalmologic apparatus 1 and the subject's eye E may be shifted in position during measurement, for example, due to involuntary movement of the eyeball, because the target of the measurement is a human who is a living body. In this way, there are also some limits to the ideal improvement of the position of the ophthalmologic apparatus 1 and the subject's Eye. Therefore, in the observation and measurement of the human eye, the ophthalmologic apparatus 1 and the subject's eye E may fall into incomplete alignment.

FIG. 3 illustrates a state in which the positional relationship between the ophthalmologic apparatus 1 and the subject's Eye is sifted by a distance Δz in the Z direction and a distance Δx in the X direction as compared to the state shown in FIG. 2. Here, if the numerical aperture g of the corneal measurement optical system 1b is made large, the focal depth decreases, and the image is more significantly deteriorated (more significant blurring occurs) relative to a defocus amount. Therefore, the numerical aperture g is desirably selected to be a somewhat small value. In the state of FIG. 3, the alignment is inappropriate, and the illumination light L1 enters the surface of the cornea E1 at an angle β with respect to a normal line orthogonal to a tangent line at a point S where the illumination light L1 enters the surface of the cornea E1. Hence, the corneal reflection light R2 reflected at the point P is reflected at the angle β with respect to the normal line. Accordingly, the illumination light L1 and the corneal reflection light R2 form an angle of 2β. As shown in FIG. 3, if the numerical aperture g of the corneal measurement optical system 1b is sufficiently smaller than the numerical aperture G of the illumination optical system 1c, and the angle 2β is sufficiently smaller than the numerical aperture G of the illumination optical system 1c, the part L1 of the illumination light (part L1-NA of the numerical aperture of the illumination optical system 1c) can contribute to the corneal reflection light R2. This enables the corneal measurement. On the other hand, if the numerical aperture g of the corneal measurement optical system 1b is not smaller than the numerical aperture G of the illumination optical system 1c, and the angle 2β is approximately equal to or larger than the numerical aperture G of the illumination optical system 1c, part L1 of the illumination light contributes only partially, or is completely unable to contribute, to the corneal reflection light R2. In such a case, the corneal measurement is hardly performed with a sufficient light intensity. Note that the angle 2β cannot be reduced below a certain value because the angle 2β is caused by the incomplete alignment determined by the characteristics of the human eye. Therefore, setting the numerical aperture g of the corneal measurement optical system 1b and the numerical aperture G of the illumination optical system 1c in a predetermined relationship makes it possible to provide an ophthalmologic apparatus that improves the measurement accuracy, while permitting variation in subject's eye shape and incomplete alignment.

Here, the numerical aperture G of the illumination optical system 1c is assumed to be approximately 0.10, and the numerical aperture g of the corneal measurement optical system 1b approximately 0.03. In this case, the numerical aperture g of the corneal measurement optical system 1b is sufficiently smaller than the numerical aperture G of the illumination optical system 1c. Therefore, the corneal measurement optical system 1b can efficiently take an image of the corneal reflection light R2 with respect to the illumination light L1, and the wavelength characteristics of the interference image can be detected with high accuracy. From the viewpoint of the accuracy of detection of the wavelength characteristics of the interference image, the numerical aperture G of the illumination optical system 1c is desirably 0.10 to 0.20, and the numerical aperture g of the corneal measurement optical system 1b is 0.01 to 0.06, more specifically, 0.02 to 0.05.

The above-described configuration can provide an ophthalmologic apparatus that optimizes the numerical apertures of the illumination optical system 1c and the corneal measurement optical system 1b, thereby improving the measurement accuracy, while permitting variation in subject's eye shape.

DESCRIPTION OF REFERENCE CHARACTERS

1: Ophthalmologic Apparatus
1a: Anterior Segment Observation Optical System
1b: Corneal Measurement Optical System
1c: Illumination Optical System
9: Control Unit
9a: Computing Unit
10: Illumination Light Source
11: Illumination System Lens
12: Filter
13: Illumination system Diaphragm
14: First Half Mirror
15: Second Half Mirror
16: Second Lens Group
17: Third Half Mirror
18: First Lens Group
19: Anterior Segment Lens
20: Anterior Segment Camera
21: Corneal Measurement System Diaphragm
22: Corneal Measurement System Lens
23: Interference Image Capturing Camera
24: Fixation Lamp

The invention claimed is:

1. An ophthalmologic apparatus, comprising:
an objective lens that faces a subject's eye;
an illumination optical system that irradiates a cornea of the subject's eye with illumination light through the objective lens; and
a corneal measurement optical system including an interference image capturing camera that takes an image of a corneal reflection light, which is a reflection of the illumination light reflected from the cornea, through the objective lens, wherein
a numerical aperture G of the illumination optical system is larger than a numerical aperture g of the corneal measurement optical system.

2. The ophthalmologic apparatus of claim 1, wherein the numerical aperture G of the illumination optical system and the numerical aperture g of the corneal measurement optical system establish the following relationship:

$$0.01/0.2 < g/G < 0.06/0.1.$$

3. The ophthalmologic apparatus of claim 1, wherein the numerical aperture G of the illumination optical system and the numerical aperture g of the corneal measurement optical system establish the following relationship:

$$0.02/0.15 < g/G < 0.05/0.1.$$

4. The ophthalmologic apparatus of claim 1, further comprising a computing unit that detects, based on a corneal reflection image of the corneal reflection light taken by the interference image capturing camera, wavelength characteristics of an interference image at each position of the corneal reflection image, thereby calculating a thickness of a tear fluid film at each position on a corneal surface.

* * * * *